(12) United States Patent
Funk et al.

(10) Patent No.: US 8,594,272 B2
(45) Date of Patent: *Nov. 26, 2013

(54) INVERSE GEOMETRY VOLUME COMPUTED TOMOGRAPHY SYSTEMS

(75) Inventors: Tobias Funk, Martinez, CA (US); Joseph Anthony Heanue, Oakland, CA (US); Waldo Stephen Hinshaw, Burlingame, CA (US); Edward Gerald Solomon, Menlo Park, CA (US); Brian Patrick Wilfley, Los Altos, CA (US)

(73) Assignee: Triple Ring Technologies, Inc., Newark, CA (US)

( * ) Notice: Subject to any disclaimer, the term of this patent is extended or adjusted under 35 U.S.C. 154(b) by 326 days.

This patent is subject to a terminal disclaimer.

(21) Appl. No.: 13/052,024

(22) Filed: Mar. 18, 2011

(65) Prior Publication Data
US 2011/0228899 A1 Sep. 22, 2011

Related U.S. Application Data

(60) Provisional application No. 61/315,780, filed on Mar. 19, 2010.

(51) Int. Cl.
*A61B 6/00* (2006.01)

(52) U.S. Cl.
USPC .................................................. 378/9; 378/10

(58) Field of Classification Search
USPC ........................................ 378/4–20, 147–153
See application file for complete search history.

(56) References Cited

U.S. PATENT DOCUMENTS

2007/0280408 A1* 12/2007 Zhang ............................. 378/10

* cited by examiner

*Primary Examiner* — Courtney Thomas
(74) *Attorney, Agent, or Firm* — Joseph T. Lin

(57) ABSTRACT

The present invention pertains to an apparatus and method for inverse geometry volume computed tomography medical imaging of a human patient. A plurality of stationary x-ray sources for producing x-ray radiation are used. A rotating collimator located between the plurality of x-ray sources and the human patient is also used. A rotating detector can also be used.

17 Claims, 8 Drawing Sheets

INVERSE GEOMETRY VOLUME COMPUTED TOMOGRAPHY SYSTEMS

RELATED U.S. APPLICATION

This application claims priority to the co-pending U.S. provisional patent application Ser. No. 61/315,780, entitled "Inverse Geometry Volume Computed Tomography Systems," with filing date Mar. 19, 2010, which is hereby incorporated by reference in its entirety.

BACKGROUND

Modern computed tomography (CT) scanners have the goal of covering a large volume of the patient in a single rotation at very fast rotation speeds. This objective is driven by demands of cardiac CT to cover the entire organ in less than a heartbeat. Impressive results have been achieved with the current generation of CT scanners. However, the downside of this development is the increased dose to the patient, the increase in scatter, and the degradation of image quality in the outer slices due to cone beam artifacts. In particular, the increased dose in medical imaging has come under scrutiny, with several published studies documenting the elevated risk of cancer resulting from the radiation involved in medical imaging.

The manufacturers of CT scanners are attempting to address dosage concerns with new developments. One common avenue being pursued is the use of photon counting detectors. Photon counting detectors have intrinsically higher detective quantum efficiency (DQE) than integrating detectors and have a bias towards lower photon energies. These qualities lead to increased image contrast, resulting in lower dose while maintaining image quality. Even more contrast enhancement and dose reduction can be achieved with the use of energy-resolving detectors. However, photon counting and energy resolving detectors are significantly more expensive than integrating detectors. This increased cost is particularly challenging for conventional CT scanners that rely on detectors with very large areas.

CT manufacturers are exploring a variety of other methods to reduce this dose while maintaining image quality. However, these improvements are expected to be minor compared to that which may be gained by an alternative CT system concept, inverse-geometry CT (IGCT). Conventional CT utilizes a single focal spot X-ray source and a large-area detector, whereas IGCT utilizes a large-area, multi-focal spot X-ray source and a small-area detector. IGCT offers higher dose efficiency and faster acquisition times than state-of-the-art conventional CT systems. Thus, IGCT has the potential to overcome disadvantages with conventional CT and significantly out-perform conventional CT scanners.

In conventional CT scanners, each projection is of the entire field of view and is obtained with a single focal-spot X-ray source and a large detector. By contrast, inverse geometry systems utilize a large-area scanned X-ray source and a field-of-view projection is composed of many narrower projections each acquired with a different detector location. The detector in an IGCT system is quite small compared to that in a conventional CT system. Thus, it is economically feasible to implement advanced yet more expensive detector technologies in IGCT. However, IGCT as currently realized in prototypes faces difficulties in implementation due to a large source array to be rotated at high speeds and significant challenges from high power and cooling requirements of the source.

What is needed is a CT imaging system capable of producing rapid high quality images. Furthermore, the CT imaging system should provide low radiation imaging.

SUMMARY

The present invention pertains to an apparatus and method for computed tomography medical imaging of a human patient. A plurality of stationary x-ray sources for producing x-ray radiation are used. A rotating collimator located between the plurality of x-ray sources and the human patient is used for projecting the x-ray radiation through the human patient. A x-ray detector is used for measuring amount of the x-ray radiation passing through the human patient and striking the detector. A method for computed tomography medical imaging of a human patient is also described. X-ray radiation from a plurality of stationary x-ray sources is produced and directed towards a collimator. The collimator is around the human patient and the amount of x-ray radiation striking a detector is measured.

These and other objects and advantages of the various embodiments of the present invention will be recognized by those of ordinary skill in the art after reading the following detailed description of the embodiments that are illustrated in the various drawing figures.

BRIEF DESCRIPTION OF THE DRAWINGS

The present invention is illustrated by way of example, and not by way of limitation, in the figures of the accompanying drawings and in which like reference numerals refer to similar elements.

DETAILED DESCRIPTION

Reference will now be made in detail to embodiments of the present invention, examples of which are illustrated in the accompanying drawings. While the invention will be described in conjunction with these embodiments, it will be understood that they are not intended to limit the invention to these embodiments. On the contrary, the invention is intended to cover alternatives, modifications and equivalents, which may be included within the spirit and scope of the invention as defined by the appended claims. Furthermore, in the following detailed description of embodiments of the present invention, numerous specific details are set forth in order to provide a thorough understanding of the present invention. However, it will be recognized by one of ordinary skill in the art that the present invention may be practiced without these specific details. In other instances, well-known methods, procedures, components, and circuits have not been described in detail as not to unnecessarily obscure aspects of the embodiments of the present invention.

Figure 1:
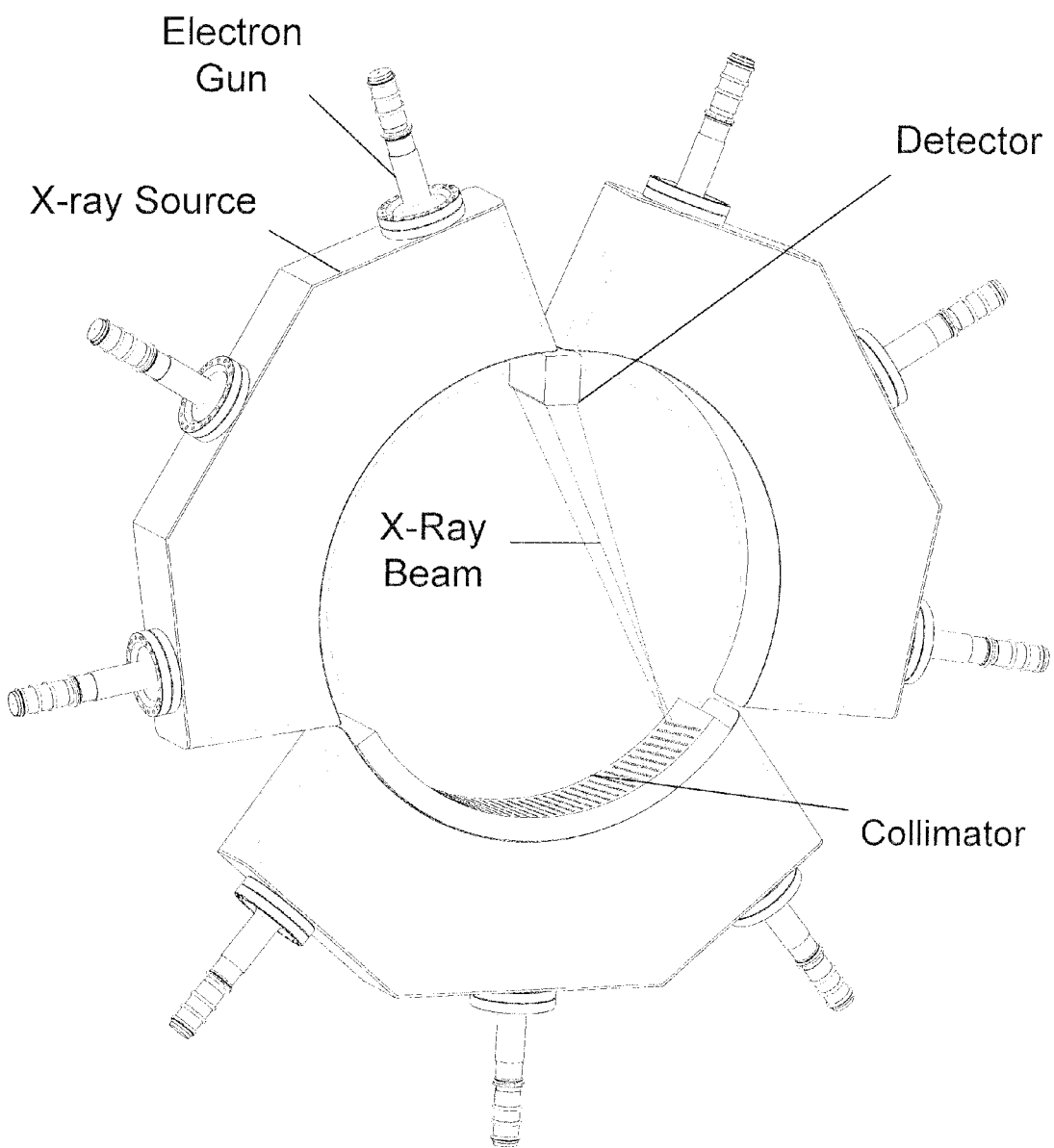
FIG. 1 is a diagram showing an exemplary fixed-source computed tomography imaging system of one embodiment of the present invention with three vacuum envelopes.

FIG. 1 is a diagram showing an exemplary fixed-source computed tomography imaging system of one embodiment of the present invention. Imaging system 100 comprises a ring of X-ray sources 101, 102, and 103 with an inner diameter of 1 m. The source ring can be made of three X-ray sources 101, 102, and 103 making a three-gap system as shown. For the three-gap system, there can be three separate source arrays, each containing three electron guns in a single vacuum envelope. Each of these source arrays can have a large-area tungsten transmission target. The source-spot locations can cover the full 360 degrees, except for a small gap of a few centimeters between each of these arrays. The axial extent of the source array can be 16 cm. There can be a fixed pre-collimator between the source arrays and the spinning ring. This pre-collimator defines the possible locations of the source-spots.

Within the ring of X-ray sources 101, 102, and 103 can be a rotating detector/collimator assembly. In one embodiment, only detector 110 and collimator 120 rotate. Collimator 120 can consist of an array of holes with each hole capable of illuminating the entire detector array. The center of the detector array can be diametrically across from the center of the collimator arc.

In operation, each row of the collimator 120 can have X-rays firing through its holes starting, for example, with the trailing hole and moving sequentially to the leading hole. The collimator rows can fire in sequence. A "super-view" can be obtained after all holes of all collimator rows have "fired". Other firing sequences are possible.

The detector elements can be read after a source-spot fires. The axial width of the detector array can also be 16 cm. By using the same axial width for both source and detector arrays there are no rays outside of the region of interest in the axial direction. Thus there is no unused exposure such as occurs in cone-beam systems.

Figure 2:
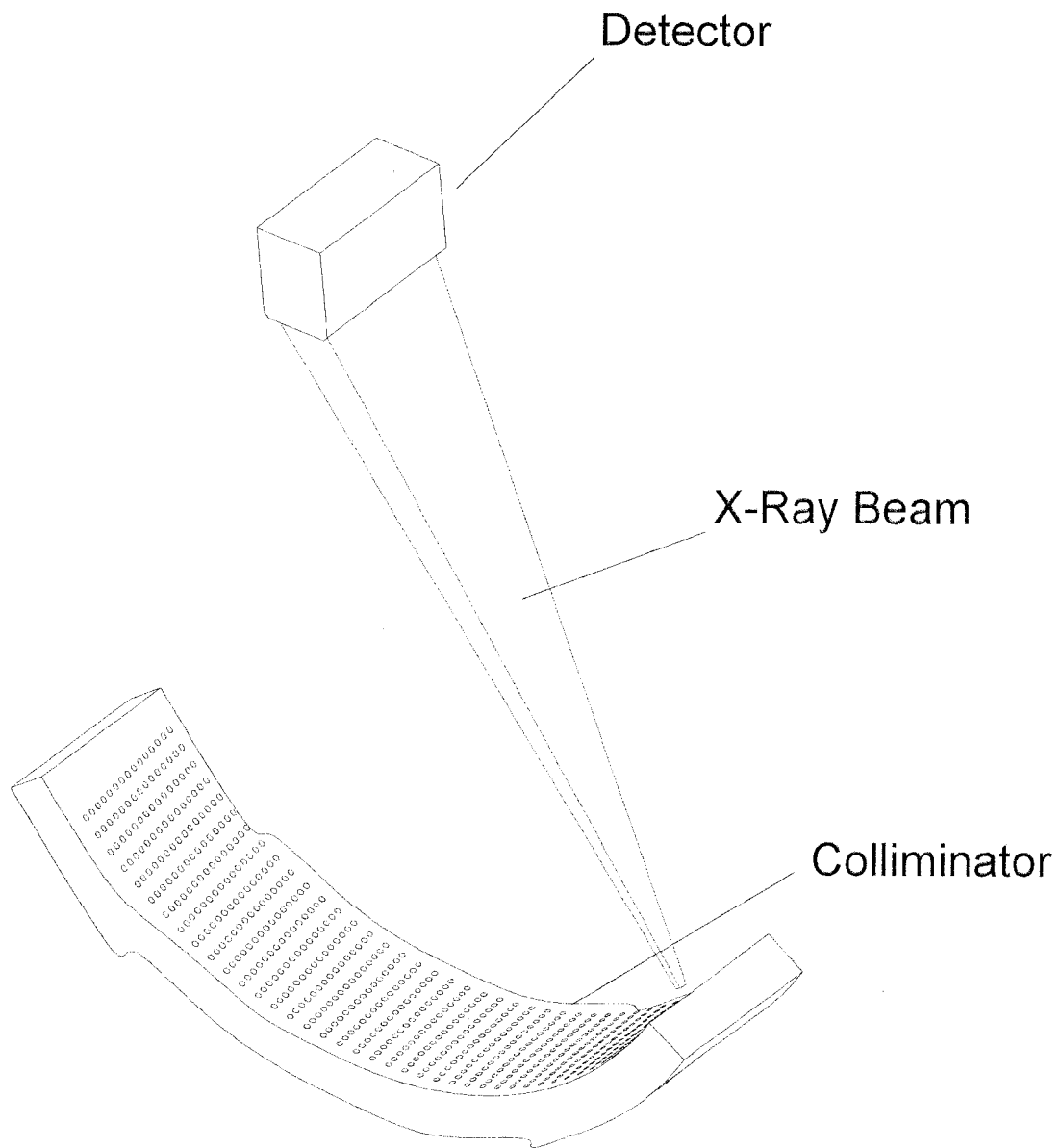
FIG. 2 is a diagram showing an exemplary isolated collimator-detector assembly of one embodiment of the present invention.

Imaging system 100 can have a large, 100 cm diameter, stationary ring of scanning X-ray source-spots. Inside the source-ring can be a rotating ring containing detector 110 and collimator 120. This rotating ring, or gantry, obtains power and outputs the detector signals through a slip-ring. FIG. 2 is a diagram showing an exemplary isolated collimator-detector assembly of one embodiment of the present invention. Collimator 220, which can be mounted opposite detector 110, can have a hole-pattern that focuses the X-rays onto detector 110. Detector 110 can be 6 cm by 16 cm and collimator 220 can span an arc of about 120 degrees and can have a width of 16 cm. Each collimator holes can illuminate the entire detector. This system design allows for rotation speeds of at least three rotations per second with image quality comparable to a conventional CT scanner.

Detector 110 can be a 6 cm by 16 cm detector. The detector ASIC can be modified to allow parallel current-integration readout and dual-energy acquisition.

Collimator 220 can be designed to attenuate 120 keV photons. It can consist of nearly 9,000 holes with a hole pitch of 2.3 mm. Each hole can be tapered and angled to project X-rays onto a 5-cm by 10-cm detector at a distance of 150 cm. Collimator 220 can also have approximately 600 holes projecting onto a 6-cm by 16-cm detector at a distance of 100 cm. Collimator 220 can be curved and have a larger area.

X-ray sources 101, 102, and 103 can be designed for continuous operation at 25 kW and at a tube voltage that can vary between 70 KVp and 120 kVp. The focal spot size can be 0.4 mm and the spot dwell time can be 1 μs with a duty cycle of 80%. The complete collimator can be scanned every 15 ms. X-ray sources 101, 102, and 103 can include a thin-film tungsten target layer deposited on a water-cooled 25-cm-diameter beryllium disc. The source power can be increased to 50 kW.

For a three-gap system, X-ray sources 101, 102, and 103 must cover a significantly larger target area. A large vacuum envelope that houses three guns in each source can be used. Each gun can illuminate a third of the target area. The use of three guns enables the entire target area to be illuminated. Different window material such as stainless steel and aluminum nitride can be used.

The projection data can be acquired as the collimator-detector assembly rotates around the patient. Collimator 120 can be located between the source array and the patient and source-spots are active only when behind collimator 120. Collimator 120 moves only a small angular increment during the time the scan of every designated hole in collimator 120 is completed. A complete scan of collimator 120 is described as a "superview". The maximum travel of detector 110 during an acquisition of a superview is one detector width. Therefore, a complete dataset can be obtained with as few as about 60 superviews.

High-weight, high-voltage, and high-power components of imaging system 100 can be removed from the challenging environment of the rotating gantry. Miniaturization of the high-voltage power supply is not required. High-power slip rings are not required. The X-ray source array can be cooled with hospital water, eliminating the conventional gantry-mounted radiator and increased air-conditioning requirement. Faster rotation times and faster volume acquisitions are possible. Overall reliability can be increased by the removal of many components, especially X-ray sources, from the high-G-force environment of the rotating gantry. A total source array area that is approximately three times larger than conventional systems can be required. However, the engineering necessary for this is greatly simplified compared to a rotating source array. Also, the cost per area for sources is significantly less than the cost per area of detectors. Thus, this can be also economically feasible.

Figure 3:
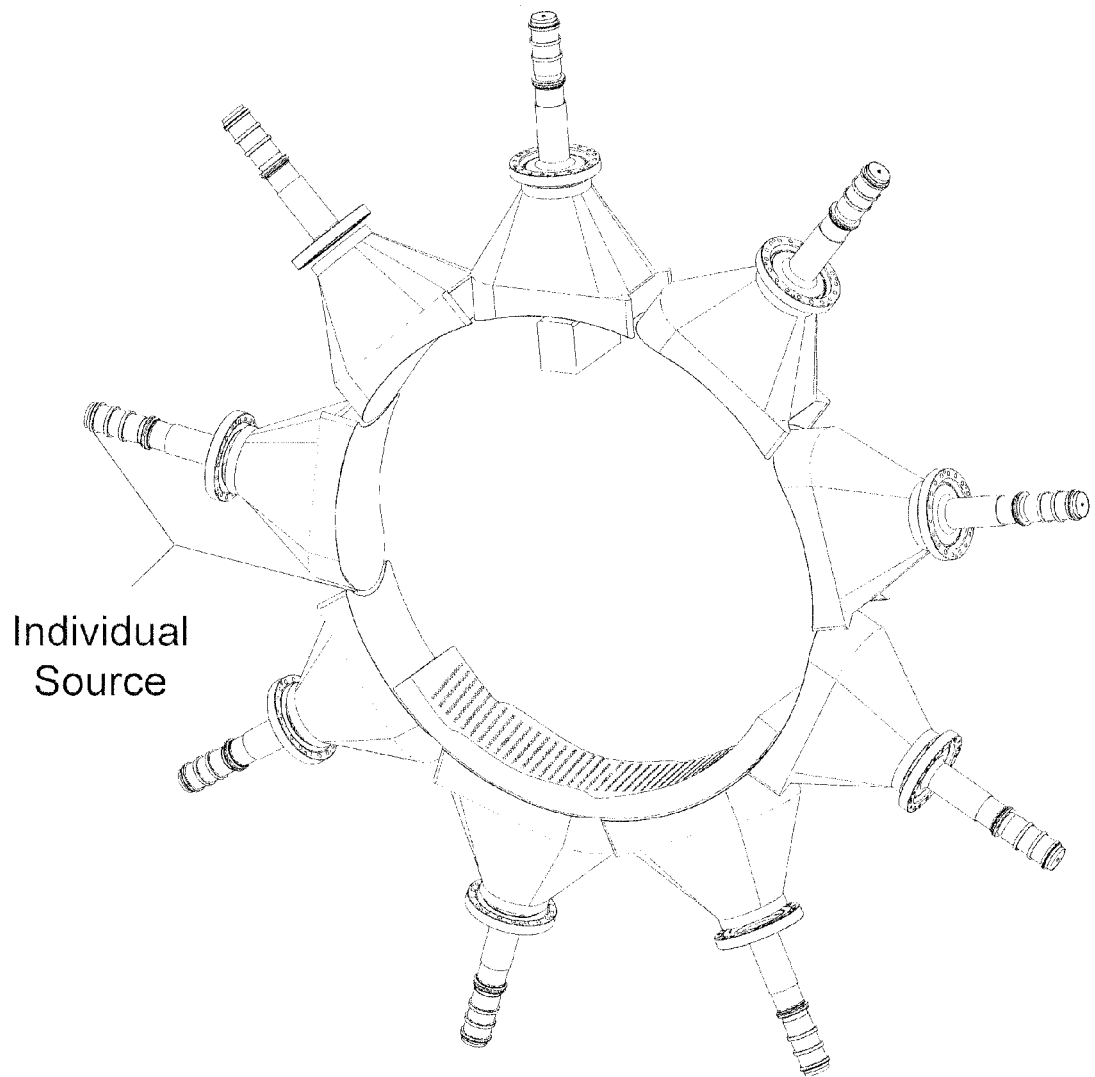
FIG. 3 is a diagram showing an exemplary fixed-source computed tomography imaging system of one embodiment of the present invention with nine vacuum envelopes.

FIG. 3 is a diagram showing an exemplary fixed-source computed tomography imaging system of one embodiment of the present invention with nine vacuum envelopes. In this embodiment, the source ring is made from nine individual X-ray sources forming a nine-gap system. There are nine separate source arrays, each containing a single electron gun in a single vacuum envelope. Each of the envelopes can have a 400 cm2 source area.

Figure 4:
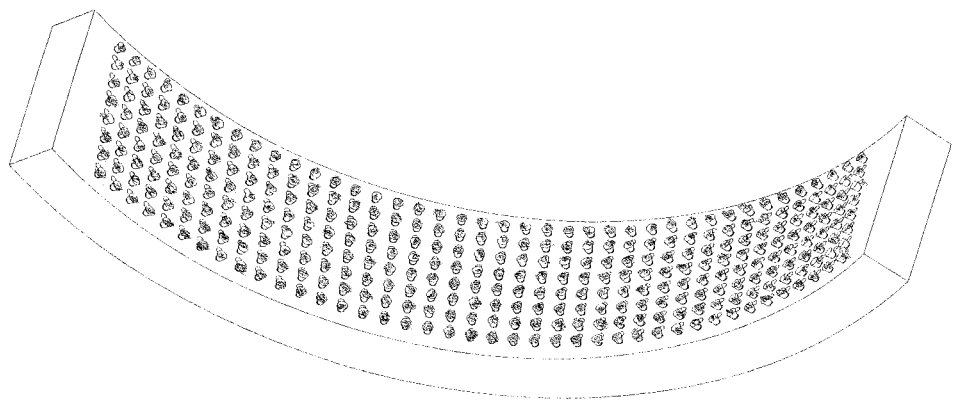
FIG. 4 is a diagram showing an exemplary uniform illumination pattern.
Figure 5:
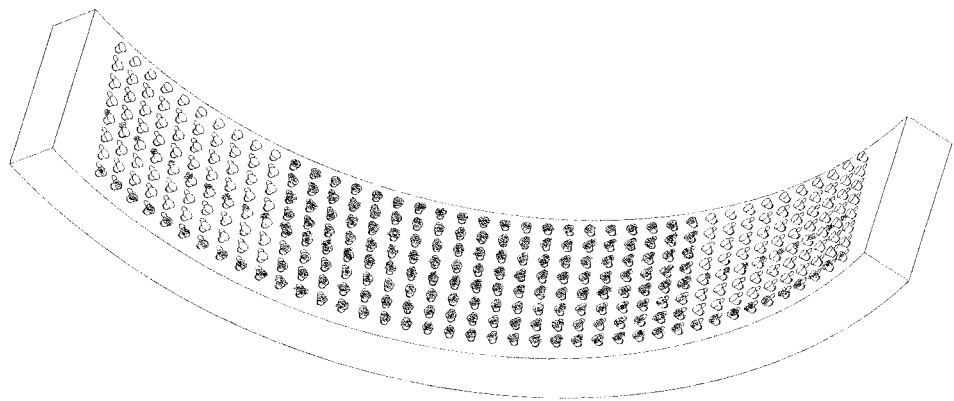
FIG. 5 is a diagram showing an exemplary illumination pattern that provides an increased flux in the central region of the collimator.
Figure 6:
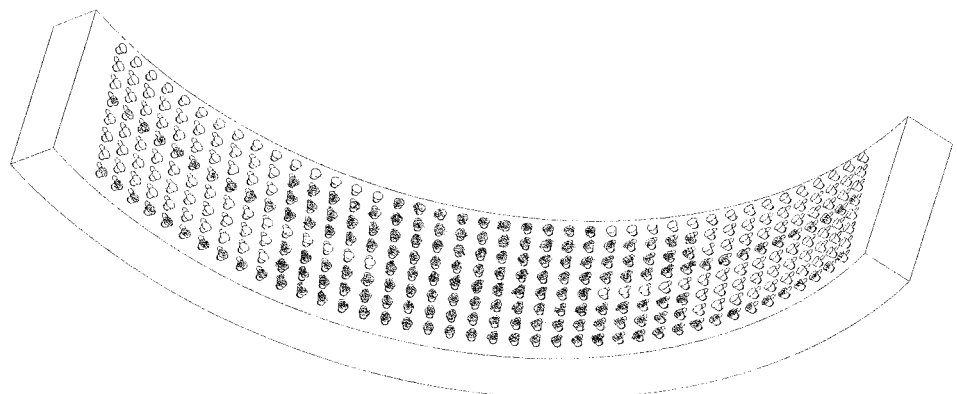
FIG. 6 is a diagram showing an exemplary illumination pattern that provides an increased flux in the central region of the collimator.

FIG. 4 is a diagram showing an exemplary uniform illumination pattern. FIG. 5 is a diagram showing an exemplary illumination pattern that provides an increased flux in the central region of the collimator. FIG. 6 is a diagram showing an exemplary illumination pattern that provides an increased flux in the central region of the collimator. FIG. 5 and FIG. 6 show patterns with increased intensity in the center. In practice the uniform and non-uniform patterns could be interleaved to ensure sampling completeness. The use of different illumination patterns can provide a two-dimensional adaptive filter. Several schemes for selecting the distribution of illumination are possible. Importantly, the illumination for one superview can be based on the results of the previous superview.

Iterative reconstruction methods can also be used. In particular, Maximum Likelihood Expectation Maximization (MLEM) is well suited for datasets from unconventional geometries. The algorithm is less prone to under-sampling artifacts and tends to reduce noise compared to standard algorithms.

One of the most critical design issues is the ability to produce enough photons to provide the desired image quality. Imaging system 100 acquires enough photons to produce an acceptable image. The detector array is 60 mm by 160 mm giving an area of about 96 cm$^2$. The duty cycle (the source-spot on time) utilized of imaging system 100 can be 80%. The source of imaging system 100 can have a power rating of 50 kW. Compared to a 85 kW tube, this reduces the number of photons by a factor of 0.59. Imaging system 100 can have a slightly shorter focus-to-detector distance giving it a factor of 1.17 advantage.

Imaging system 100 does not rely on the anti-scatter grids used in conventional CT systems to reduce scattered radiation in the projection images. As discussed earlier, imaging system 100 takes advantage of the significantly smaller detector compared to a conventional system. Scatter scales approximately with the detector size assuming a constant distance between patient and detector. The smaller detector of imaging system 100 can be a significant advantage as the amount of scatter scales with the illuminated volume that, for a fixed object, is proportional to the detector area. The amount of scatter can be less than 10% for imaging system 100 while for a conventional system scatter exceeds 40% In a conventional system, scatter is managed with an anti-scatter grid, whereas in imaging system 100, an anti-scatter grid will not be necessary. The efficiency is about 75%. Imaging system 100 can have a significantly lower scatter fraction and can be operated without an anti-scatter grid, giving a photon advantage of 1.33.

Detector 110 can be photon counting, having an intrinsic DQE advantage of 20%. Additionally, photon counting detectors have a bias towards lower energies giving another 20% advantage. Thus, fewer photons are needed for the same image quality and can be counted as a (virtual) flux increase of a factor 1.44.

The transmission anode of imaging system 100 can provide 1.7 times as many photons for the same current as the more traditional steep-angle reflection anode.

Because imaging system 100 can adjust the number of photons depending upon the thickness of the object on a view-by-view, or even beam-by-beam, basis, a significant increase in maximum number of photons can be obtained. An average increase of a factor of 4 can be achieved.

The following table summarizes the cumulative advantages and disadvantages, and shows that the number of available photons is comparable to that of a standard system.

| IGCT/Standard | Cumulative | IGCT property relative to standard |
| --- | --- | --- |
| 0.15 | 0.15 | smaller detector area |
| 0.80 | 0.12 | lower duty cycle for IGCT |
| 0.59 | 0.07 | less tube power |
| 1.17 | 0.08 | shorter source-detector distance |
| 1.33 | 0.11 | operation without AS grid |
| 1.44 | 0.16 | photon-counting detector |
| 1.70 | 0.27 | transmission anode |
| 4.00 | 1.08 | virtual bow-tie |

The duty cycle can be increased to 100%. Imaging system 100 can use multiple tubes that can be alternated thus filling in the off-time of a single source. In addition, both iterative reconstruction and energy resolving detectors can improve performance. Overall, imaging system 100 can increase the effective number of photons by more than a factor of two.

Some of the effects discussed previously convert directly into dose savings to the patient. Imaging system 100 does not rely on the anti-scatter grids used in conventional CT systems. Anti-scatter grids are positioned after the patient and also prevent a significant percentage of the radiation from reaching the detector. Thus removing the anti-scatter grid reduces the dose to the patient. The omission of anti-scatter grids, and similarly, the removal of the dead-space between detector elements, leads to about a 25% improved dose efficiency.

The implementation of an adaptive filter can be used with inverse geometry CT and imaging system 100. The effective intensity of each source-spot-to-detector beam can be adjusted depending on the patient thickness, or attenuation, for that beam. This adaptive approach also minimizes irradiation where no body parts are present. A dose saving on the order of a factor of two can be achieved. Photon counting detectors provide an additional dose savings of a factor of 1.44.

The combined dose saving with imaging system 100 is almost a factor of 4. Even further dose savings can be achieved with the use of an energy resolving detector and iterative reconstruction methods. Imaging system 100 can be used only to scan the organ of interest and thereby further reduce the dose to the patient.

Figure 7:
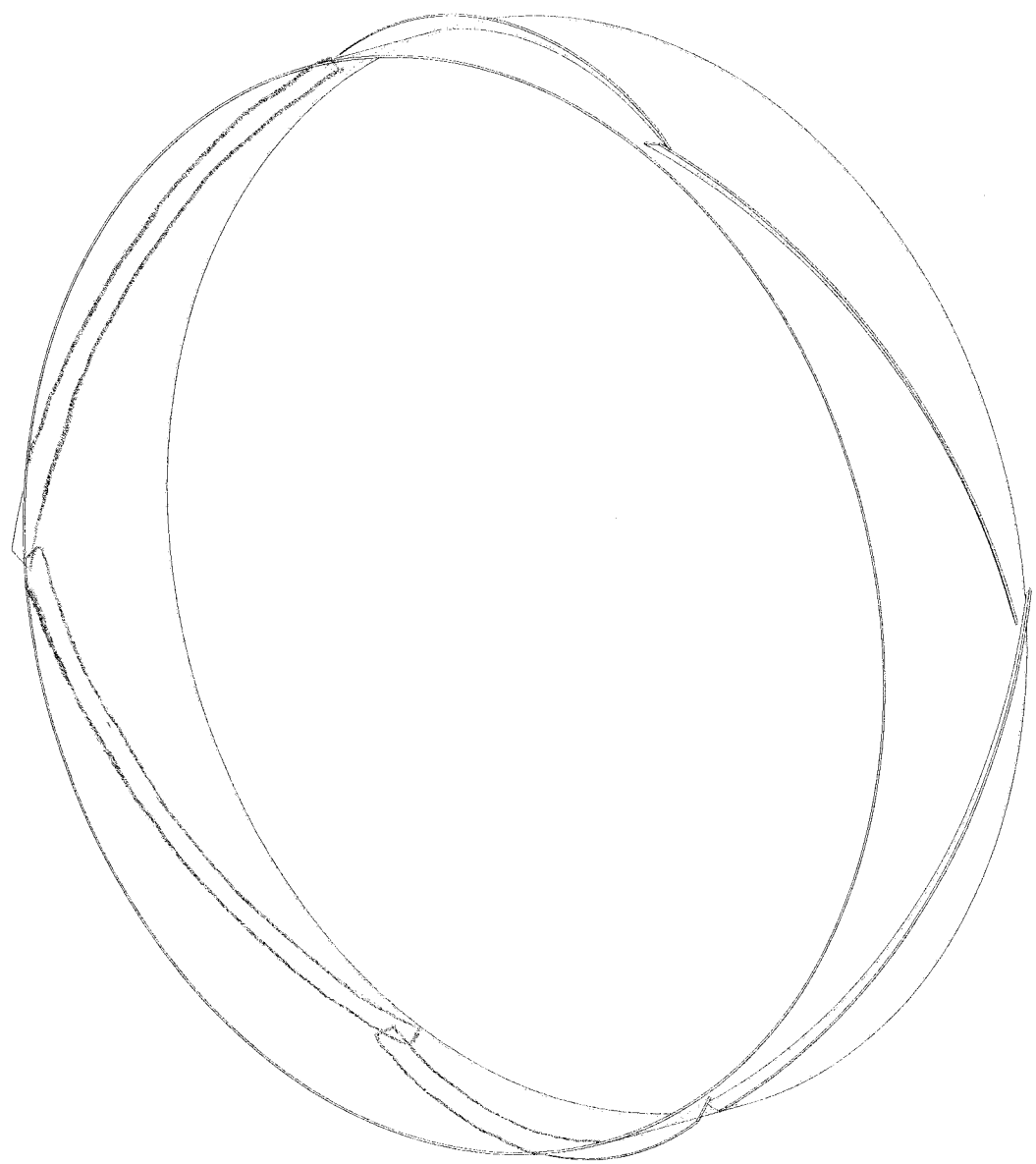
FIG. 7 is a diagram showing an exemplary source ring with linear sources of one embodiment of the present invention.

FIG. 7 is a diagram showing an exemplary source ring with linear sources of one embodiment of the present invention. Rather than using a two-dimensional array of sources, the source ring uses lines of sources. These linear sources can be constructed using either transmission targets or reflection targets. An array of linear X-ray tubes is arranged in a ring. Detector-collimator assembly rotates inside the ring.

Figure 8:
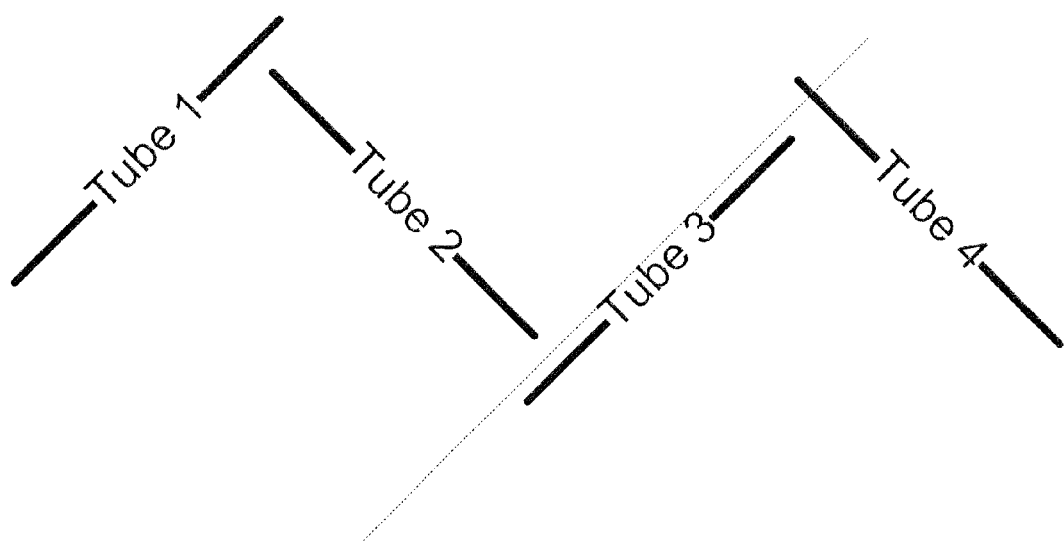
FIG. 8 is a diagram showing an exemplary arrangement of sources of one embodiment of the present invention.

FIG. 8 is a diagram showing an exemplary arrangement of sources of one embodiment of the present invention. An array of linear x-ray tubes is arranged in a ring. Detector-collimator assembly rotates inside the ring. This arrangement of source-spots can achieve complete sampling as the gap between any two linear sources is covered by a third linear source as shown in FIG. 8. Every plane intersecting the ring also intersects a source trajectory. As an example, although the dashed line lies in the gap between tube 2 and 3, it intersects tube 4 of FIG. 8. Another advantage is that the tube target, whether transmission or reflection, can be at a steep angle with respect to the X-ray beam. This allows a line-focus electron beam to be used which, in turn, enables a four-fold increase in tube power. The area source approach has advantages with the heat loading of the target and that implementation of the virtual bowtie is easier.

Imaging system 100 can have numerous advantages compared to conventional CT systems. Imaging system 100 can have lower dose and can be four-fold more dose-efficient than conventional systems. Imaging system 100 can have faster volume acquisition with scan times less than 300 msec. Imaging system 100 can perform whole-organ imaging with no table translation and no cone-beam artifacts. Data can be reconstructed using existing algorithms. Thus, advantages include fast acquisition and the reduction of dose, artifacts, and cost. Image quality can be comparable to standard CT and also have a significant margin to exceed current performance. Complete datasets can be produced and a variety of reconstruction algorithms can be used for efficient reconstruction.

The foregoing descriptions of specific embodiments of the present invention have been presented for purposes of illustration and description. They are not intended to be exhaustive or to limit the invention to the precise forms disclosed, and many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the claims appended hereto and their equivalents.

What is claimed is:

1. A computed tomography x-ray imaging system for imaging a human patient comprising:
    a plurality of stationary x-ray sources for producing x-ray radiation;
    a rotating collimator located between said plurality of x-ray sources and said human patient for projecting said x-ray radiation through said human patient; and
    an x-ray detector for measuring amount of said x-ray radiation passing through said human patient and striking said detector.

2. The computed tomography x-ray imaging system of claim 1 wherein said plurality of stationary x-ray sources are arranged in a ring around said human patient.

3. The computed tomography x-ray imaging system of claim 2 wherein said plurality of stationary x-ray sources are scanned x-ray sources.

4. The computed tomography x-ray imaging system of claim 1 wherein said x-ray detector rotates at a speed of at least three rotations per second.

5. The computed tomography x-ray imaging system of claim 1 further comprising:
    three vacuum envelopes wherein each of said vacuum envelopes comprising three of said plurality of x-ray sources.

6. The computed tomography x-ray imaging system of claim 1 wherein said plurality of stationary x-ray sources is an array of linear x-ray tubes.

7. The computed tomography x-ray imaging system of claim 1 wherein said collimator spans an arc in the range of 120 degrees and less.

8. The computed tomography x-ray imaging system of claim 1 further comprising:
    nine vacuum envelopes wherein each of said nine vacuum envelopes comprising one of said plurality of x-ray sources.

9. The computed tomography x-ray imaging system of claim 1 wherein said collimator is scanned with said x-ray radiation every 15 milliseconds.

10. The computed tomography x-ray imaging system of claim 1 wherein said collimator spans an arc of about 120 degrees.

11. The computed tomography x-ray imaging system of claim 1 wherein said x-ray detector is capable of rotating around said patient.

12. The computed tomography x-ray imaging system of claim 1 wherein said x-ray detector has an axial width in the range of 16 cm and less.

13. The computed tomography x-ray imaging system of claim 1 wherein said x-ray detector has a length in the range of 16 cm and less.

14. The computed tomography x-ray imaging system of claim 1 wherein said x-ray detector has a width in the range of 5 cm and less.

15. A method for producing a computed tomography x-ray image of a human patient comprising:
    producing x-ray radiation from a plurality of stationary x-ray sources;
    directing said x-ray radiation towards a collimator;
    rotating said collimator around said human patient; and
    measuring amount of said x-ray radiation striking a detector.

16. The method of claim 15 further comprising:
    rotating said detector around said human patient.

17. The method of claim 15 further comprising:
    scanning an electron beam over a target to produce said x-ray radiation.

* * * * *